US008686186B2

(12) United States Patent
Ure

(10) Patent No.: US 8,686,186 B2
(45) Date of Patent: Apr. 1, 2014

(54) METHODS, PROCESSES, AND SYSTEMS FOR TREATING AND PURIFYING CRUDE TEREPHTHALIC ACID AND ASSOCIATED PROCESS STREAMS

(75) Inventor: Alan Macpherson Ure, Cleveland (GB)

(73) Assignee: INVISTA North America S.ar.l., Wilmington, DE (US)

( * ) Notice: Subject to any disclaimer, the term of this patent is extended or adjusted under 35 U.S.C. 154(b) by 215 days.

(21) Appl. No.: 13/265,991

(22) PCT Filed: Apr. 22, 2010

(86) PCT No.: PCT/GB2010/000806
§ 371 (c)(1), (2), (4) Date: Dec. 13, 2011

(87) PCT Pub. No.: WO2010/122304
PCT Pub. Date: Oct. 28, 2010

(65) Prior Publication Data

US 2012/0142962 A1 Jun. 7, 2012

Related U.S. Application Data

(60) Provisional application No. 61/172,247, filed on Apr. 24, 2009.

(51) Int. Cl.
*C07C 51/43* (2006.01)

(52) U.S. Cl.
USPC ............ 562/485; 562/486; 562/494

(58) Field of Classification Search
USPC ............ 562/485, 486, 494
See application file for complete search history.

(56) References Cited

U.S. PATENT DOCUMENTS

| | | | | |
|---|---|---|---|---|
| 3,497,552 | A * | 2/1970 | Olsen | 562/486 |
| 3,850,983 | A | 11/1974 | Park | |
| 4,833,269 | A | 5/1989 | Schroeder | |
| 5,304,676 | A | 4/1994 | Hindmarsh et al. | |
| 5,741,927 | A * | 4/1998 | Parker et al. | 562/486 |
| 6,689,903 | B2 * | 2/2004 | O'Meadhra et al. | 562/486 |
| 2006/0014979 | A1 | 1/2006 | Numata et al. | |

FOREIGN PATENT DOCUMENTS

| | | |
|---|---|---|
| JP | 52128344 | 1/2006 |
| WO | 9923055 | 5/1999 |

* cited by examiner

*Primary Examiner* — Brian J Davis
(74) *Attorney, Agent, or Firm* — Stephen J. Mackenzie

(57) ABSTRACT

Embodiments of the present disclosure include methods or processes for purifying CTA, systems for purifying CTA, methods or processes for cooling mother liquor streams, systems for cooling mother liquor streams, methods or processes for treating mother liquor solids, systems for treating mother liquor solids, and the like.

13 Claims, 4 Drawing Sheets

METHODS, PROCESSES, AND SYSTEMS FOR TREATING AND PURIFYING CRUDE TEREPHTHALIC ACID AND ASSOCIATED PROCESS STREAMS

CROSS-REFERENCE TO RELATED APPLICATION

This application claims benefit of priority from U.S. Provisional Application No. 61/172,247 filed Apr. 29, 2004.

FIELD OF THE DISCLOSURE

The following disclosure relates to methods of recycling chemicals.

BACKGROUND

Purified terephthalic acid is produced in a two stage process. In the first stage, the oxidation plant, crude terephthalic acid (CTA) is produced by the air oxidation of paraxylene in a solvent (e.g., acetic acid and water) using a homogeneous catalyst. The catalyst can be one or more heavy metal compounds (e.g., cobalt and/or manganese compounds or other heavy metals such as vanadium, chromium, iron, molybdenum, a lanthanide such as cerium, zirconium, hafnium and/or nickel and an oxidation promoter). The metal compound can take any of the forms of catalyst that have been used in the liquid phase oxidation of aromatic carboxylic acid precursor (s) in aliphatic carboxylic acid solvent (e.g., bromide, bromoalkanoates or alkanoates (usually C1-C4 alkanoates, such as acetates)). The oxidation promoter, where employed, can be in the form of elemental bromine, ionic bromide (e.g., HBr, NaBr, KBr, NH4Br) and/or organic bromide (e.g., bromobenzenes, benzyl-bromide, mono- and dibromoacetic acid, bromoacetyl bromide, tetrabromoethane, ethylene-di-bromide, etc.). Alternatively, the oxidation promoter can include a ketone (e.g., methylethylketone) or aldehyde (e.g., acetaldehyde).

The reaction temperature of about 150-210° C. or about 160-200° C. The oxidation is typically carried out in one, two or three vessels in series, and multiple reactors can be used in parallel for each step. Reactor vessels are typically agitated vessels, where the agitation is achieved by a combination of a mechanical agitation, plus the agitation effect of the air being added.

The main impurity in crude terephthalic acid is 4 carboxy benzaldehyde, a reaction intermediate and terephthalic acid precursor. This is present in the CTA at a concentration of about 1000-4000 ppm or about 2500-3500 ppm. Other intermediates and contaminants present in the CTA include paratoluic acid and organic compounds contributing to color (colored chemicals) such as 2,6 dicarboxyfluorenone. The following references describe in detail the range of colored compounds present in PTA and CTA; U.S. Pat. No. 4,626,598, U.S. Pat. No. 3,850,983, and U.S. Pat. No. 4,833,269. These colored compounds are formed in the oxidation reactor. Some of the colored compounds remain in solution and are removed from the oxidation via a byproduct purge route, but a significant proportion are precipitated in the CTA crystals and transferred in the CTA to the purification stage of the process.

The second stage of the production process is the purification of the CTA by catalytic hydrogenation in aqueous solution. Typically, CTA is dissolved in water at high pressure (70-90 bar(a)) and high temperature (275-290° C.), and hydrogenated over a fixed bed catalyst of palladium supported on carbon. In the hydrogenation process the main impurity 4 carboxy-benzaldehyde (4CBA) is reacted to paratoluic acid. Also, numerous colored compounds are hydrogenated. An example of a colored compound is 2,6 dicarboxyfluorenone, and this is converted to 2,6 dicarboxyfluorene. Whilst this has some contribution to the color in the PTA, it is less colored than 2,6 dicarboxyfluorenone present in CTA.

The resulting solution is cooled as it passes through a series of four to six crystallizers, where the majority of the paratoluic acid remains in solution and the purified terephthalic acid (PTA) is crystallized. The resulting slurry (at a temperature of 140-160° C.) is then fed to solid liquid separation device(s), such as a decanter centrifuge or rotary pressure filter. The PTA is separated from the mother liquor stream. The mother liquor stream includes 4-carboxy benzaldehyde and paratoluic acid. The mother liquor stream also contains PTA fines that slip through the separation device. These components represent a significant yield loss from the process, and it is desirable to recycle these components to the oxidation stage of the process. The mother liquor also includes hydrogenated color compounds. Approximately 50% of the hydrogenated color compounds remain with the PTA, so the remaining 50% remain in the mother liquor. Thus, methods to recycle 4-carboxy benzaldehyde and paratoluic acid and the PTA fines have been described previously (e.g., U.S. Pat. No. 5,304,676 and JP 52-128344) but these have not solved the further problems defined here.

In order to recover the paratoluic and terephthalic acids, the mother liquor must be cooled to precipitate the organic acids, which are then separated from the mother liquor. A method of producing this separation is to flash-cool the stream by reducing the pressure to atmospheric pressure, where the temperature of the mother liquor is reduced to around 100° C. Further cooling is then desirable to enable further recovery of terephthalic and paratoluic acids.

SUMMARY

Further cooling, as referenced above, has been attempted using a number of methods that are not desirable because they are not practical technically or chemically, are expensive because they require large capital investments, have high operating costs, or combinations thereof. Therefore there is a need to overcome these and/or other deficiencies of current technologies.

One exemplary method of cooling a mother liquor stream, among others, includes: providing the mother liquor stream having a temperature of about 140 to 170° C. at a pressure of about 3.5 to 8 bar(a), wherein the mother liquor stream is a saturated solution including terephthalic acid and paratoluic acid in water, and contains less than about 1% w/w of fine solid particles of terephthalic acid; introducing the mother liquor stream to a flash tank where the pressure in the flash tank is about atmospheric pressure, for example about 1 bar (a), wherein steam from the mother liquor stream is generated and removed from the flash tank; flowing the mother liquor stream to a cooler in a first pipe, wherein at a mixture point prior to the mother liquor stream entering the cooler, the mother liquor stream is mixed with a secondary mother liquor stream at about 40 to 60° C., wherein the mixture of the mother liquor stream and the secondary mother liquor stream forms the mother liquor mixture, wherein the mother liquor mixture is at about 60 to 80° C. after mixing the mother liquor stream and the secondary mother liquor stream, wherein prior to entering the cooler, a portion of the terephthalic acid and the paratoluic acid are precipitated from the mother liquor mixture; cooling the mother liquor mixture to about 40 to 60°

C. in the cooler; flowing the mother liquor mixture out of the cooler towards a filter; flowing a first portion of the mother liquor mixture to the filter; and flowing a second portion of the mother liquor mixture, referred to as the secondary mother liquor stream, into a recycling pipe, wherein the recycling pipe intersects the first pipe at the mixture point.

One exemplary method of cooling a mother liquor stream, among others, includes: providing the mother liquor stream having a temperature of about 140 to 170° C. at a pressure of about 3.5 to 8 bar(a), wherein the mother liquor stream is a saturated solution including terephthalic acid and paratoluic acid in water, and contains less than about 1% w/w of fine solid particles of terephthalic acid; introducing the mother liquor stream to a flash tank where the pressure is about 1 bar(a), where the temperature of the mother liquor stream is reduced to about 100° C., wherein steam from the mother liquor stream is generated and removed from the flash tank; flowing the mother liquor stream to a cooler in a first pipe, wherein at a mixture point prior to the mother liquor stream entering the cooler, the mother liquor stream is mixed with a secondary mother liquor stream at about 40 to 60° C., wherein the mixture of the mother liquor stream and the secondary mother liquor stream forms the mother liquor mixture, wherein the mother liquor mixture is at about 60 to 80° C. after mixing the mother liquor stream and the secondary mother liquor stream, wherein prior to entering the cooler a portion of the terephthalic acid and the paratoluic acid are precipitated from the mother liquor mixture; cooling the mother liquor mixture to about 40 to 60° C. in the cooler; flowing the mother liquor mixture out of the cooler towards a filter; flowing a first portion of the mother liquor mixture to the filter; flowing a second portion of the mother liquor mixture, referred to as the secondary mother liquor stream, into a recycling pipe, wherein the recycling pipe intersects the first pipe at the mixture point; filtering the first portion of the mother liquor mixture using the filter, wherein precipitates of each of the terephthalic acid and the paratoluic acid are removed from the mother liquor mixture; mixing the precipitates of each of the terephthalic acid and the paratoluic acid in acetic acid to form an acetic acid slurry of precipitates; introducing the acetic acid slurry of precipitates to a stream of acetic acid at about 150 to 170° C. to form a recycling stream that includes the dissolved precipitates of each of the terephthalic acid and the paratoluic acid; and introducing the recycling stream to an oxidation feed stream or an oxidation reactor.

BRIEF DESCRIPTION OF THE DRAWINGS

Many aspects of this disclosure can be better understood with reference to the following drawings. The components in the drawings are not necessarily to scale.

DETAILED DESCRIPTION

Figure 1:
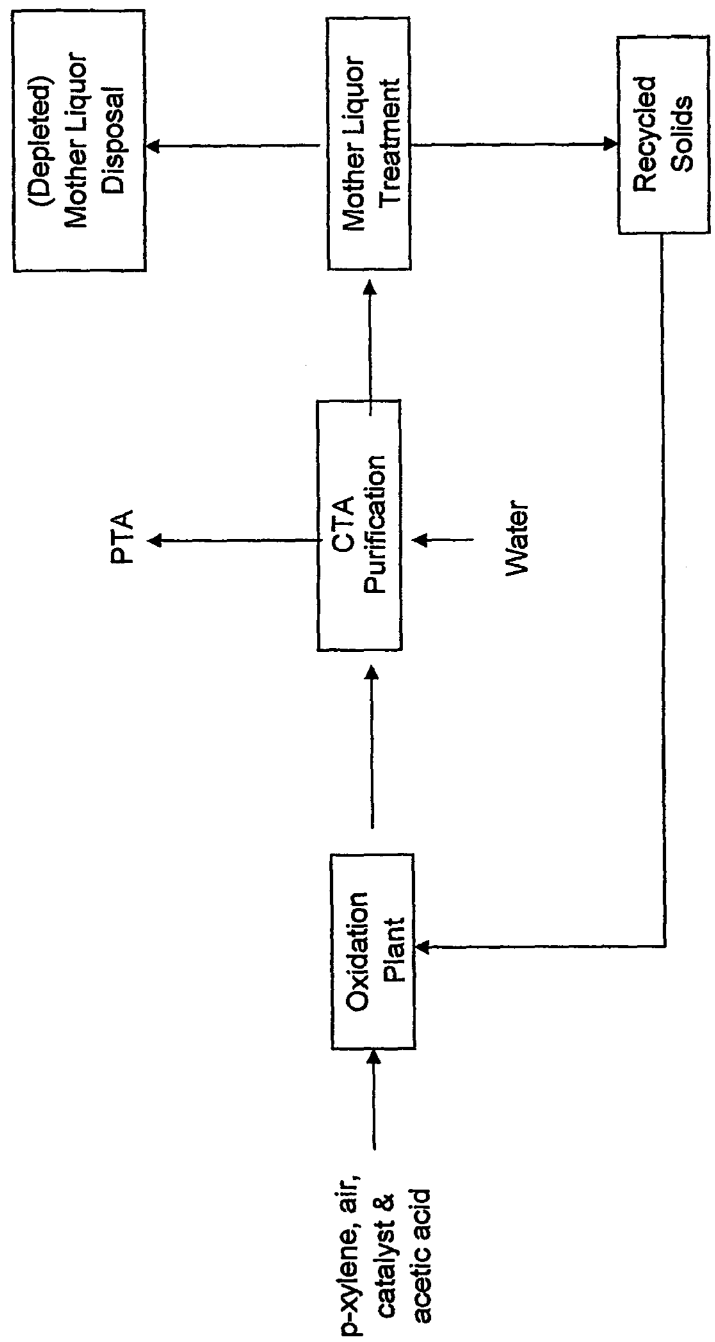
FIG. 1 illustrates a schematic block diagram of a process for the production of purified terephthalic acid (PTA).

Before the present disclosure is described in greater detail, it is to be understood that this disclosure is not limited to particular embodiments described, as such can, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Embodiments of the present disclosure will employ, unless otherwise indicated, techniques of chemistry, chemical engineering, chemical recycling, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar(a).

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "mother liquor solids" refers to the solids collected following precipitation from the residual mother liquor resulting from the separation of the purified terephthalic acid from the slurry generated during the crystallization stage of the terephthalic acid purification process.

Discussion

Embodiments of the present disclosure include methods or processes for purifying CTA, systems for purifying CTA, methods or processes for cooling mother liquor streams, systems for cooling mother liquor streams, methods or processes for treating mother liquor solids, systems for treating mother liquor solids, and the like.

FIG. 1 is a block diagram of a method or process for the production of purified terephthalic acid. Crude terephthalic acid (CTA) is produced by the air oxidation of paraxylene, using a homogeneous catalyst in aqueous acetic acid solvent. The air used for oxidation contains molecular oxygen that can be enriched or depleted in comparison with atmospheric air, prior to feeding to an oxidation reactor. The resulting slurry of CTA from the oxidation reactor(s), comprising CTA, oxidation catalyst, reaction intermediates and by products, including color compounds, is typically fed to one or more vessels to reduce the pressure and temperature of the process stream. The CTA solid is separated from the oxidation process mother liquor and, optionally, dried from the oxidation solvent. The CTA solid is then mixed with water to form the CTA purification feed stream, prior to purification of the CTA in the second stage of the PTA manufacturing process. The CTA purification process/system can include a number of stages including, but not limited to, CTA re-slurrying stage, slurry heating and CTA dissolution stage, catalytic hydrogenation stage, crystallization stage, filtration stage, solvent recovery stage, drying stage, a mother liquor stream treatment stage, a mother liquor solid treatment stage, and the like.

The process produces purified terephthalic acid in a crystallized form and a mother liquor stream. The mother liquor stream comprises paratoluic acid as well as PTA fine particles (also referred to as "fines") and hydrogenated color compounds. In an embodiment, the mother liquor stream is a saturated solution including terephthalic acid and paratoluic acid in water, and contains less than about 1% w/w of fine solid particles of terephthalic acid. As mentioned above, the process includes a method for treating the mother liquor stream to recover the paratoluic and terephthalic acids (precipitates of paratoluic and terephthalic acids). Once the solids (the mother liquor solids or precipitates) are recovered and separated from the resulting mother liquor, the solids can be recycled and mixed with the oxidation feed stream and/or directly introduced into the first stage of the CTA purification. The mother liquor stream (depleted) remaining after the mother liquor solids are recovered can be treated as is appropriate (effluent stream).

Figure 2:
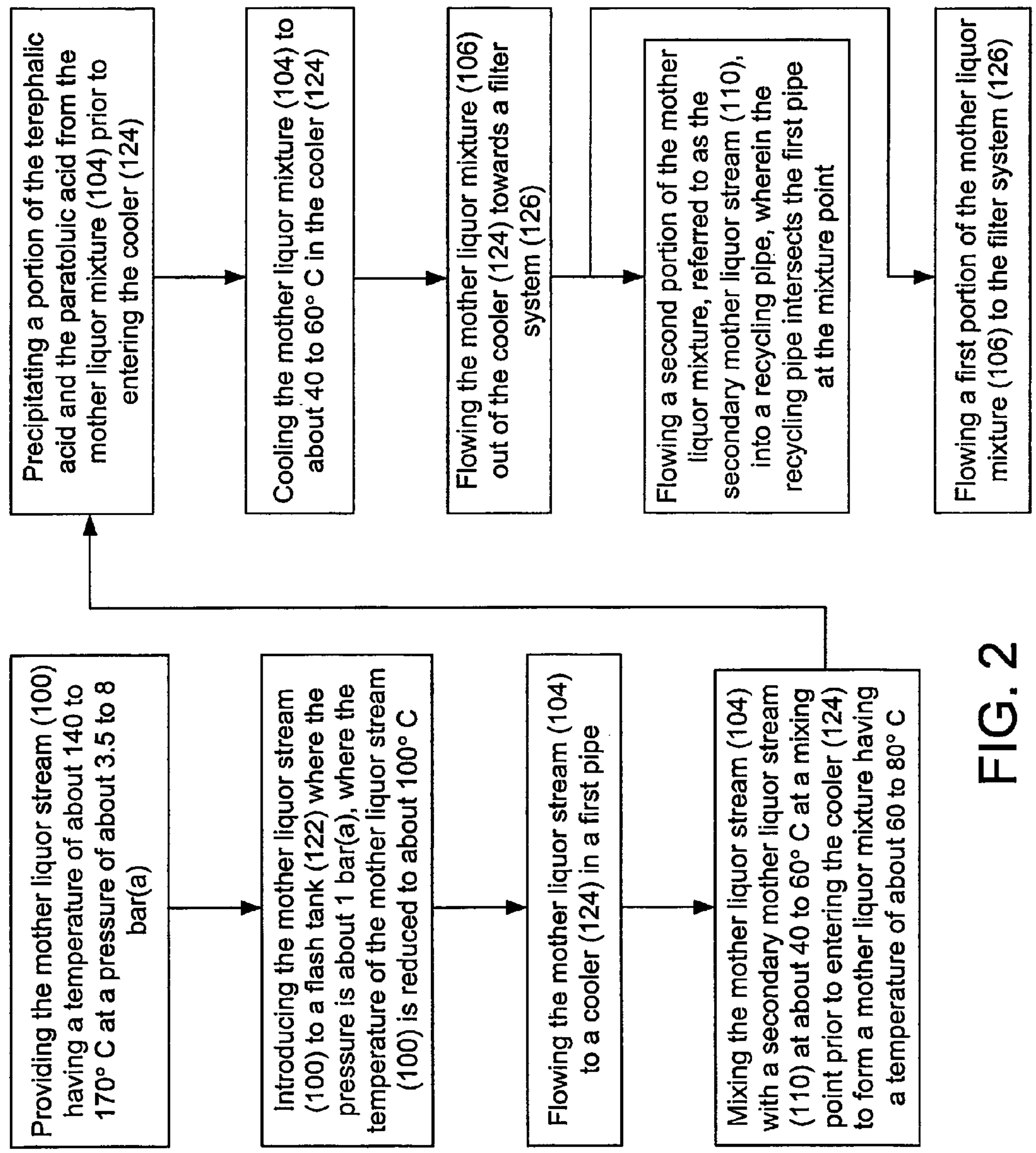
FIG. 2 illustrates a flow chart of an embodiment of a method for processing mother liquor streams.
Figure 3:
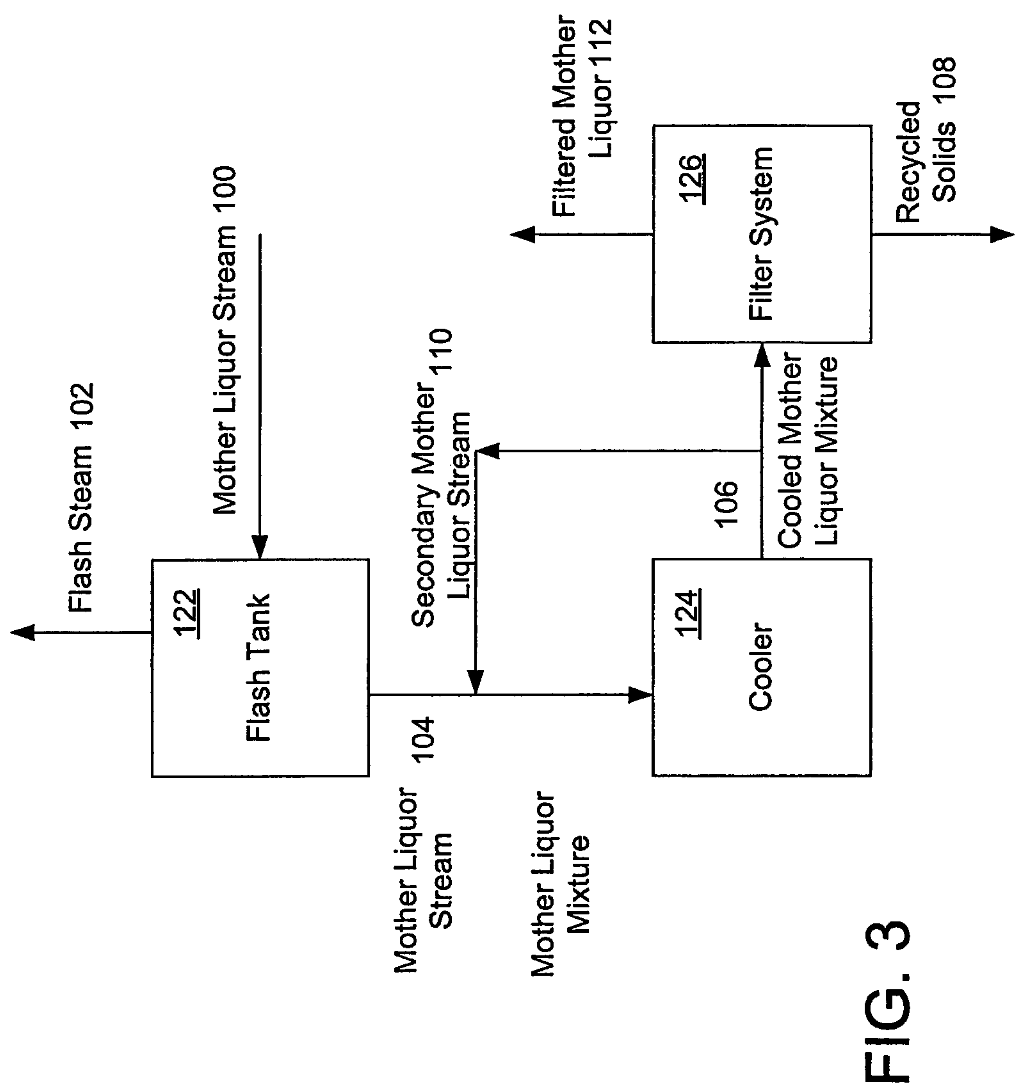
FIG. 3 illustrates a schematic diagram of a method for processing mother liquor streams.

As noted above, the process includes methods for treating the mother liquor stream to recover the paratoluic and terephthalic acids. As described in the flow chart shown in FIG. 2 and in the schematic shown in FIG. 3, a mother liquor stream (100) is provided after separation of the purified terephthalic acid (PTA), in the purification process. In an embodiment, the mother liquor stream (100) can have a temperature of about 140 to 170° C. or about 145 to 155° C. In an embodiment, the mother liquor stream (100) can have a pressure of about 3.5 to 8 bar(a) or about 4 to 5.5 bar(a). The mother liquor stream (100) is introduced to a flash tank (122) where the pressure is typically atmospheric pressure, about 1 bar(a) and/or where the temperature of the mother liquor stream (100) is reduced to about 100° C. As a result a substantial quantity of steam (102) is evaporated due to isenthalpic flashing, and this leaves or is removed from the flash tank (122). Next, the mother liquor stream (104) is flowed to a cooler (124) via a first pipe or other flow structure.

Prior to entering the cooler (124), the mother liquor stream (104) is mixed with a secondary mother liquor stream (110). The secondary mother liquor stream (110) is about 40 to 60° C. or about 45 to 55° C. The secondary mother liquor stream (110) is introduced to the mother liquor stream (104) at a mixing point. The mixing point is at a position where the first pipe and a recycling pipe intersect and can take various forms such as Y, L, or T intersection with or without additional agitation. The mixture of the two streams forms a mother liquor mixture having a temperature of about 60 to 80° C. or about 65 to 75° C. The mother liquor mixture is not given a numeral indication in FIG. 3 for reasons of clarity. The flow rate of the secondary mother liquor stream can be adjusted so that the temperature of the mother liquor mixture is about 60 to 80° C. or about 65 to 75° C. In an embodiment, the flow rate of the secondary mother liquor stream is about 60% of the mixed mother liquor flow rate. As a result of the mixing and the reduction in the temperature, a portion of the terephthalic acid and/or the paratoluic acid is precipitated from the mother liquor mixture prior to entering the cooler (124). In an embodiment, the amount of the terephthalic acid and/or the paratoluic acid solid can be about 75 to 85% or about 79 to 83%, of the total of terephthalic acid and/or the paratoluic acid in the mother liquor mixture after mixing.

Subsequently, the mother liquor mixture including the precipitates enters the cooler (124) and is cooled to about 40 to 60° C. or about 45 to 55° C. Terephthalic acid and/or the paratoluic acid not precipitated previously can be precipitated out during this cooling procedure. The cooler (124) can be a low fouling high shear heat exchanger such as, but not limited to, a spiral heat exchanger (such as one sold by Alfa-Laval), a spiratube heat exchanger (such as one sold by HRS Spiratube), a shell and tube heat exchanger or a combination thereof. An advantage of using a high shear cooler (124) is that precipitates do not foul or do not substantially foul the components of the cooler (124). A possible explanation for this result is that the stream is flowing at a high flow rate and any precipitants that may form on and/or coat the components are self-cleaned by the high flow rate. In addition, since a portion of the precipitants are formed prior to entering the cooler (124), the amount of fouling is reduced because the amount of precipitation occurring in the cooler (124) is reduced and/or the precipitants flowing at high flow rates can strip off coatings on the components of the cooler (124). In an embodiment, the flow rate is about 1 to 4 m/s or about 1 to 3 m/s.

In an embodiment, the spiral heat exchanger includes at least two separate and adjacent spirally configured flow conduits typically separated by a single wall. A cooling medium flows through one conduit and the mother liquor mixture, including precipitates, flows through the alternate conduit and is cooled by heat transfer to the cooling medium across the separating wall between the flow channels. The cooling medium is typically cooling water and the flow rate can be adjusted to control the exit temperature of the mother liquor mixture. The extent of cooling also controls the additional precipitates generated in the cooler (124). The flow-path for the mother liquor mixture in the spiral heat exchanger is configured so the whole of the flowing volume traverses the conduit at essentially the same velocity, with no significant horizontal flow regions or significant stagnant volumes. Additionally, the minimum dimension of the flow channel is configured to avoid precipitates interrupting the flow-path of the mother liquor mixture as it cools. The velocity of the mother liquor mixture through the conduits is maintained so that precipitates formed prior to entering the cooler or generated within the cooler are entrained in the flowing mother liquor mixture and exit the cooler with the cooled mother liquor mixture.

In an embodiment, the shell and tube heat exchanger includes a series of essentially parallel tubes through which the mother liquor mixture including precipitates flows and is cooled by heat transfer to a cooling medium flowing externally to the tubes. Although the cross-sectional flow area inside the tubes is frequently circular, alternative configurations can be used to enhance heat transfer, increase shear rate of the flowing medium or other parameter to improve operation or performance of the cooler (124). The variations in flow cross section can also vary continuously or irregularly over the length of the tube and can include changes in surface area of the tube wall, number of flow passages or projections into the flow-path of the mother liquor mixture. The heads of the heat exchanger, the inlet and outlet are designed to prevent precipitated solids settling or accumulating to prevent flow of the mother liquor mixture and even distribution of the mother liquor mixture through each of the tubes of the heat exchanger, regardless of the number of tube-side passes. In an embodiment, for a shell and tube heat exchanger mechanical agitation can be used additionally inside the tubes to prevent accumulation of solids formed prior to entering the cooler (124) or generated within the cooler (124) from the mother liquor mixture.

Once the mother liquor mixture is cooled in the cooler (124), the mother liquor mixture (106) is flowed toward a filter system (126) in a flow pipe. The mother liquor mixture (106) is at about 40 to 60° C. or about 45 to 55° C. Prior to entering the filter system (126), a recycling pipe intersects the flow pipe. A first portion of the mother liquor mixture (106) is flowed to the filter system (126), and a second portion of the mother liquor mixture (106) is flowed in the recycling pipe. Once the second portion is in the recycling pipe, the stream is referred to as the "secondary mother liquor stream (110)". As mentioned above, the recycling pipe intersects the first pipe at the mixing point. Thus, the second portion of the mother liquor mixture (110) is flowed through the recycling pipe to mix with the mother liquor stream (104) at the mixing point. The first portion is about 35 to 45% w/w or about 38 to 42% w/w of the mother liquor mixture (106). The second stream is about 55 to 65% w/w or about 58 to 62% w/w of the mother liquor mixture (106).

Figure 4:
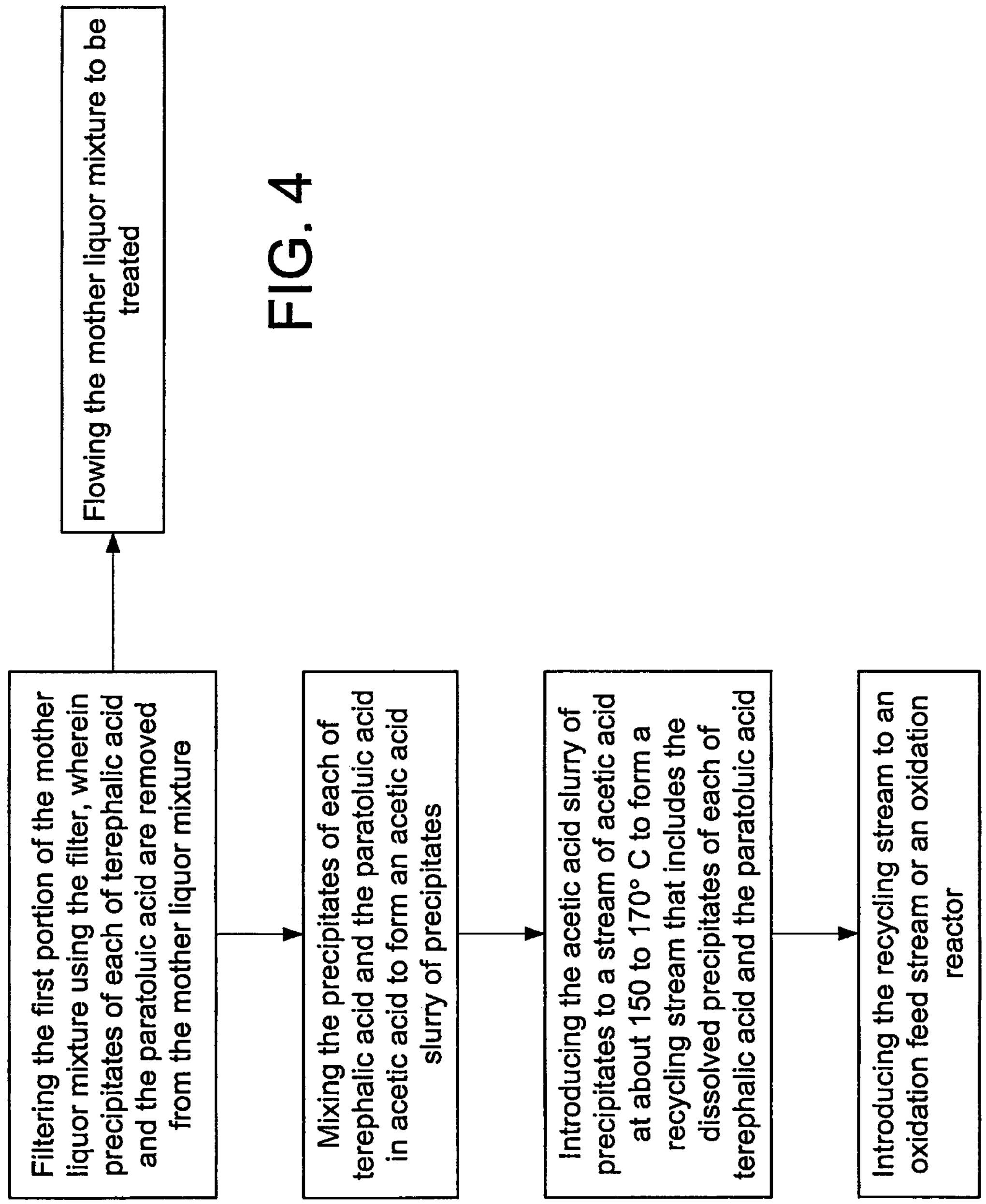
FIG. 4 illustrates a flow chart of an embodiment of a method for processing solids (e.g., precipitates) separated from a mother liquor mixture stream.

As shown in FIG. 4 and generally in FIG. 1, the first portion of the mother liquor mixture can be filtered by the filter system (126). The precipitates of mother liquor solids comprising terephthalic acid and/or the paratoluic acid (as well as other precipitates) are captured by the filter and separated from the remaining mother liquor mixture. The remaining mother liquor mixture can be processed further as needed or disposed of to effluent treatment. The filter system (126) includes a pressure filter in which build up of a filter cake on a filter medium occurs in such a way that the filter cake is itself instrumental in filtering the solids-containing liquid. Various forms of filtration processes are suitable, e.g., a pressure vessel equipped with a candle filter or filters (such as one sold by Dr. Muller AG). The filter system also includes a receiver vessel in which precipitates discharged from the filter are re-slurried in acetic acid and a control system. The system can optionally include a number of buffer vessels in order to facilitate smooth operation of the system.

In an embodiment, the precipitates are mixed with acetic acid to form an acetic acid slurry of precipitates. The flowrate of acetic acid is controlled to ensure that the acetic acid slurry of precipitates contains about 10 to 20% w/w solids. Subsequently, the acetic acid slurry of precipitates are introduced to a stream of acetic acid at about 150 to 170° C. or about 155 to 165° C., to form a recycling stream. The rate of addition of the slurry of precipitates is controlled, so as to ensure that the concentration of components such as terephthalic acid and paratoluic acid as well as other components (e.g., hydrogenated color compounds) are below their solubility limits in the recycling stream. In an embodiment, the rate of addition of the slurry of precipitates is controlled so that the concentration is below their limit of solubility in the aqueous acetic acid solvent at about 150-170° C. In an embodiment, the concentration of the slurry of precipitates in the recycling stream can be below the solubility limit of the precipitates. In an embodiment, the concentration of the slurry of precipitates in the recycling stream can be less than 10000 ppm w/w of precipitates in the recycle stream. In an embodiment, the concentration of the slurry of precipitates in the recycling stream can be about 2000 ppm w/w in the recycling stream.

In an embodiment, the water content of the recycling stream is about 10 to 20% w/w water or about 10 to 15% w/w water. In an embodiment, the introduction of the acetic acid slurry of precipitates to the stream of acetic acid at about 150 to 170° C. is conducted at a rate so that the concentration of the terephthalic acid is less than 2000 ppm w/w in the recycling stream up to about 10,000 ppm w/w in about 20% water.

It should be noted that mixing the acetic acid slurry of precipitates with the stream of acetic acid produces at least two surprising and unexpected results when compared to simply feeding the filtered precipitates directly to the oxidation reactor and/or via the main oxidation feed stream. First, the recycled solids, including the paratoluic acid, dissolve in the heated acetic acid and can be fully oxidized to terephthalic acid in the oxidation reactor. As a result, the recycled paratoluic acid appears to be prevented from contaminating the CTA in the oxidation reactor and the full benefit of recycling the recycled solids to improve the overall conversion from p-xylene to the desired product terephthalic acid can be achieved. The improvement is equivalent to a savings of about 1-2 kg of paraxylene per tonne (metric ton) of PTA product.

Second, the hydrogenated color components in the recycle solids also dissolve in the hot acetic acid solvent and are oxidized to form oxidized color compounds in the oxidation reactor. For example, 2,6 dicarboxyfluorene is oxidized to 2,6 dicarboxyfluorenone. The oxidized color components are more colored than the hydrogenated color components, but the proportion of them ending up in the CTA is much less than the proportion of hydrogenated color components that ends up in the CTA for a similar process not including embodiments described herein. A surprising benefit of the present disclosure is that, despite the oxidized color compounds being present in the oxidation reactor, the overall color of the CTA improves by about 1-4 DCMY units compared to a similar process not including the embodiments described herein. On the purification plant, an improved CTA color allows the hydrogenation reactor to operate at lower pressure and results in a lower usage of hydrogen.

It should be noted that FIGS. 1 to 4 may not include all of the various components used in each system, method, or process. For example, one or more fluid pumps can be used to cause the streams to flow through the system or process at one or more flow rates and at one or more pressures.

EXAMPLES

Samples of CTA were taken from an operating plant utilizing an embodiment of the present disclosure described herein and from an operating plant where the filtered precipitates were fed with the main oxidation reactor feed. The average concentration of 2,6 dicarboxyfluorene and 2,6 dicarboxyfluorenone in the samples of CTA, and their associated DCMY color were as follows:

| CTA samples | | | |
|---|---|---|---|
| | 2,6 dicarboxy-fluorene (ppm w/w) | 2,6 dicarboxy-fluorenone (ppm w/w) | DCMY color |
| Plant using embodiment | <2 | 52 | 28.0 |
| Plant not using embodiment | 9 | 134 | 31.9 |

This data shows that less 2,6 dicarboxyfluorene and 2,6 dicarboxyfluorenone was incorporated into the CTA on the plant using an embodiment of the invention, and the resulting benefit in DCMY color.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

Many variations and modifications can be made to the above-described embodiments. All such modifications and variations are intended to be included herein within the scope of this disclosure and protected by the following claims.

What is claimed is:

1. A method of cooling a mother liquor stream, comprising:
- providing the mother liquor stream having a temperature of about 140 to 170° C. at a pressure of about 3.5 to 8 bar(a), wherein the mother liquor stream is a saturated solution including terephthalic acid and paratoluic acid in water, and contains less than about 1% w/w of fine solid particles of terephthalic acid;
- introducing the mother liquor stream to a flash tank where the pressure in the flash tank is about atmospheric pressure, wherein steam from the mother liquor stream is generated and removed from the flash tank;
- flowing the mother liquor stream to a cooler in a first pipe, wherein at a mixture point prior to the mother liquor stream entering the cooler, the mother liquor stream is mixed with a secondary mother liquor stream at about 40 to 60° C., wherein the mixture of the mother liquor stream and the secondary mother liquor stream forms the mother liquor mixture, wherein the mother liquor mixture is at about 60 to 80° C. after mixing the mother liquor stream and the secondary mother liquor stream, wherein prior to entering the cooler, a portion of the terephthalic acid and the paratoluic acid are precipitated from the mother liquor mixture;
- cooling the mother liquor mixture to about 40 to 60° C. in the cooler;
- flowing the mother liquor mixture out of the cooler towards a filter;
- flowing a first portion of the mother liquor mixture to the filter; and
- flowing a second portion of the mother liquor mixture, referred to as the secondary mother liquor stream, into a recycling pipe, wherein the recycling pipe intersects the first pipe at the mixture point.

2. The method of claim 1, wherein the velocity of the mother liquor mixture in the cooler is about 1 to 4 m/s.

3. The method of claim 1, wherein the cooler is a low fouling, high shear cooler.

4. The method of claim 3, wherein the cooler is a spiral cooler.

5. The method of claim 4, wherein the spiral cooler includes plates and the plates are spaced apart by about 5 to 20 mm.

6. The method of claim 3, wherein the cooler is a shell and tube cooler.

7. The method of claim 1, wherein the first portion of the mother liquor mixture is about 35 to 45% w/w of the mother liquor stream and the second portion of the mother liquor mixture is about 55 to 65% w/w of the mother liquor stream.

8. The method of claim 1, wherein the portion of the terephthalic acid and the paratoluic acid precipitated is about 75 to 85% w/w.

9. The method of claim 1, further comprising:
- filtering the first portion of the mother liquor mixture using the filter, wherein precipitates of each of the terephthalic acid and the paratoluic acid are removed from the mother liquor mixture;
- mixing the precipitates of each of the terephthalic acid and the paratoluic acid in acetic acid to form an acetic acid slurry of precipitates;
- introducing the acetic acid slurry of precipitates to a stream of acetic acid at about 150 to 170° C. to form a recycling stream that includes the dissolved precipitates of each of the terephthalic acid and the paratoluic acid; and
- introducing the recycling stream to an oxidation feed stream or an oxidation reactor.

10. The method of claim 9, wherein the water content of the recycling stream is about 10 to 20% w/w water.

11. The method of claim 9, wherein the concentration of the terephthalic acid is below the solubility limit of terephthalic acid in the recycling stream.

12. The method of claim 9, wherein the introduction of the acetic acid slurry of precipitates to the stream of acetic acid at about 150 to 170° C. is conducted at a rate so that the concentration of the terephthalic acid is less than 10,000 ppm w/w in the recycling stream.

13. A method of cooling a mother liquor stream, comprising:
- providing the mother liquor stream having a temperature of about 140 to 170° C. at a pressure of about 3.5 to 8 bar(a), wherein the mother liquor stream is a saturated solution including terephthalic acid and paratoluic acid in water, and contains less than about 1% w/w of fine solid particles of terephthalic acid;
- introducing the mother liquor stream to a flash tank where the pressure is about 1 bar(a), where the temperature of the mother liquor stream is reduced to about 100° C., wherein steam from the mother liquor stream is generated and removed from the flash tank;
- flowing the mother liquor stream to a cooler in a first pipe, wherein at a mixture point prior to the mother liquor stream entering the cooler, the mother liquor stream is mixed with a secondary mother liquor stream at about 40 to 60° C., wherein the mixture of the mother liquor stream and the secondary mother liquor stream forms the mother liquor mixture, wherein the mother liquor mixture is at about 60 to 80° C. after mixing the mother liquor stream and the secondary mother liquor stream, wherein prior to entering the cooler a portion of the terephthalic acid and the paratoluic acid are precipitated from the mother liquor mixture;
- cooling the mother liquor mixture to about 40 to 60° C. in the cooler;
- flowing the mother liquor mixture out of the cooler towards a filter;
- flowing a first portion of the mother liquor mixture to the filter;

flowing a second portion of the mother liquor mixture, referred to as the secondary mother liquor stream, into a recycling pipe, wherein the recycling pipe intersects the first pipe at the mixture point;

filtering the first portion of the mother liquor mixture using the filter, wherein precipitates of each of terephthalic acid and the paratoluic acid are removed from the mother liquor mixture;

mixing the precipitates of each of terephthalic acid and the paratoluic acid in acetic acid to form an acetic acid slurry of precipitates;

introducing the acetic acid slurry of precipitates to a stream of acetic acid at about 150 to 170° C. to form a recycling stream that includes the dissolved precipitates of each of terephthalic acid and the paratoluic acid; and introducing the recycling stream to an oxidation feed stream or an oxidation reactor.

* * * * *